United States Patent
Roychowdhury et al.

(10) Patent No.: US 6,295,714 B1
(45) Date of Patent: Oct. 2, 2001

(54) PROCESS FOR FABRICATING A PROSTHESIS

(75) Inventors: Suranjan Roychowdhury, Minnetonka, MN (US); Leonard Pinchuk, Miami, FL (US); Eugen Hofmann, Zürich; Susanne Hankh, Villmergen, both of (CH); Michael G. O'Connor, Blaine, MN (US); Jennifer E. Raeder-Devens, St. Paul, MN (US); Jeannine B. Baden, Rogers, MN (US); Daniel J. Klima, St. Cloud, MN (US)

(73) Assignee: Schneider (USA) Inc, Plymouth, MN (US)

( * ) Notice: Subject to any disclaimer, the term of this patent is extended or adjusted under 35 U.S.C. 154(b) by 0 days.

(21) Appl. No.: 09/510,209

(22) Filed: Feb. 22, 2000

Related U.S. Application Data

(62) Division of application No. 09/060,695, filed on Apr. 15, 1999, now Pat. No. 6,027,529.
(60) Provisional application No. 60/042,226, filed on Apr. 15, 1997.

(51) Int. Cl.$^7$ .................................................. B21D 39/00
(52) U.S. Cl. ........................ 29/516; 623/1.12; 623/1.15; 623/1.19; 29/417
(58) Field of Search ............................ 29/417, 516, 517; 623/1, 12, 1.12, 1.15, 1.19, 1.2, 1.22, 1.53; 606/1, 108, 151, 198; 228/110.1, 112.1, 182, 255; 219/121.6, 121.64, 121.63, 80, 82

(56) References Cited

U.S. PATENT DOCUMENTS

| | | | |
|---|---|---|---|
| 4,655,771 | 4/1987 | Wallsten | 623/1 |
| 4,776,337 | 10/1988 | Palmaz | 128/343 |
| 5,015,253 | 5/1991 | McGregor | 623/1 |
| 5,026,377 | 6/1991 | Burton et al. | 606/108 |
| 5,171,262 | 12/1992 | McGregor | 623/1 |
| 5,226,913 | * 7/1993 | Pinchuk | 623/1 |
| 5,304,200 | 4/1994 | Spaulding | 606/198 |
| 5,328,469 | 7/1994 | Coletti | 604/96 |
| 5,437,083 | * 8/1995 | Williams et al. | 29/235 |
| 5,546,646 | * 8/1996 | Williams et al. | 29/516 |
| 5,549,663 | 8/1996 | Cottone, Jr. | 623/1 |
| 5,575,818 | 11/1996 | Pinchuk | 623/1 |
| 5,591,222 | * 1/1997 | Susawa et al. | 606/195 |
| 5,628,787 | * 5/1997 | Mayer | 606/198 |
| 5,716,396 | 2/1998 | Williams, Jr. | 623/1 |
| 5,725,519 | * 3/1998 | Penner et al. | 606/198 |
| 5,738,674 | * 4/1998 | Williams et al. | 606/1 |
| 5,746,764 | * 5/1998 | Green et al. | 606/108 |
| 5,824,043 | * 10/1998 | Cottone, Jr. | 606/195 |
| 5,893,867 | * 4/1999 | Bagaoisan et al. | 606/198 |
| B1 4,655,771 | 9/1996 | Wallsten | 623/1 |

FOREIGN PATENT DOCUMENTS 98107386  2/1998  (WO) .............................. A61F/2/06

* cited by examiner

*Primary Examiner*—S. Thomas Hughes
*Assistant Examiner*—Jermie E. Cozart
(74) *Attorney, Agent, or Firm*—Larkin, Hoffman, Daly & Lindgren, Ltd.; Frederick W. Niebuhr, Esq.

(57) ABSTRACT

A body implantable stent is formed of a plurality of strands arranged in two sets of coaxial helices, wound in opposite directions to form multiple crossings. At selected crossings, the adjacent strands are welded to one another, while at the remaining crossings the strands are free for limited movement relative to one another. The welds are formed in patterns that preferably enhance radial strength and rigidity, while having a minimal impact on axial bending flexibility. Preferred weld patterns in this regard include rings or circumferential rows, and helices, particularly with a steeper pitch than that of the strands. Stent fabrication preferably involves resistance welding at the crossings, and use of a tool to reuniformly compress the stent around and against the distal end region of a balloon catheter used later to deliver the stent to a treatment site.

29 Claims, 6 Drawing Sheets

PROCESS FOR FABRICATING A PROSTHESIS

This is a divisional of prior application Ser. No. 09/060,695, filed Apr. 15, 1998, now U.S. Pat. No. 6,027,529.

This Application claims the benefit of priority of Provisional Application No. 60/042,226 entitled "Methods of Joining Stent Wires," filed Apr. 15, 1997.

BACKGROUND OF THE INVENTION

The present invention relates to body implantable prostheses, and more particularly to stents and stent grafts insertable into blood vessels and other body lumens and radially expandable against surrounding tissue for fixation.

A variety of treatment and diagnostic procedures involve devices intralumenally implanted into the body of the patient. Among these devices are stents, such as disclosed in U.S. Pat. No. 4,655,771 (Wallsten). The Wallsten prostheses or stents are tubular, braided structures formed of helically wound thread elements. The stents are deployed using a delivery catheter such as disclosed in U.S. Pat. No. 5,027,377 (Burton, et al.). With the stent positioned at the intended treatment site, an outer tube of the delivery catheter is withdrawn, allowing the stent to radially expand into a substantially conforming surface contact with a blood vessel wall or other lumen-defining tissue.

An alternative stent construction features plastically deformable strands or members, usually formed of a ductile metal. Examples of such stents are shown in U.S. Pat. No. 4,776,337 (Palmaz), and U.S. Pat. No. 5,716,396 (Williams, Jr.). Such stents do not require outer tubes or other features to maintain them in a reduced-radius state during delivery. However, radial expansion at the treatment site requires an expandable balloon or other feature for enlarging the stent.

Regardless of whether stents are self-expanding or plastically deformable, they characteristically have an open mesh or open frame construction, or otherwise are formed with multiple openings to facilitate radial enlargements and reductions, and to allow tissue in-growth. Further, either type of stent can be used to support a substantially fluid impermeable material, frequently but not necessarily elastic, to provide a stent graft for shunting blood or other body fluids past a weakened or damaged area, e.g. an aneurysm.

Stents and stent grafts of either type must be constructed in view of two competing considerations: flexibility for axial bending, and radial rigidity or strength. Axial bending, i.e. bending of the stent about any number of transverse (radial) axes along its length, is necessary for translumenal delivery through curved, even serpentine vessels and other passages. Radial stiffness and strength are needed after delivery and radial enlargement, to maintain the lumen open against any radial forces from surrounding tissue. In stent constructions featuring helically wound strands, there also is a need to balance radial strength and rigidity with the desire to minimize the degree of axial shortening that accompanies any radial enlargement. Radial strength is enhanced by a large braid angle, i.e. a relatively steep pitch of the strand helix relative to the longitudinal stent axis about which the helical strands are wound. Conversely, a reduced braid angle or pitch involves less axial shortening for a given amount of radial enlargement. Joining all of the intersections or crossings of strands has been suggested to enhance resiliency in self-expanding stents. This, however, increases the resistance to axial bending, making the device difficult to maneuver through tortuous passages, and imparting a high axial stiffness after radial enlargement.

The aforementioned '396 patent discloses a structure intended to provide radial support while allowing axial bending flexibility. In particular, a helically wound strand of malleable material has a repeating pattern of undulations or bendable segments, each with a semi-circular portion and two straight leg portions. Adjacent turns of the helix are joined by at least one weld joining two of the semi-circular portions. Aside from the complexity of shaping the strand to produce the undulations, an undesirable structural feature resides in the welding of successive turns, in that structural integrity for resisting axial tension depends entirely on the welds.

Other problems, more particular to plastically deformable stents, concern the tendency to recoil, i.e. radially contract, after their radial enlargement. This creates the need to over-enlarge the stent or stent graft, to insure its fixation. Also, a radial compression of the plastically deformable stent, typically about an expandable balloon at the distal tip of a catheter, is necessary prior to deployment. Such compression must be done with care, to insure a uniform radial contraction, and to avoid irregularities or distortions in the stent structure.

Therefore, it is an object of the present invention to provide a body insertable prosthesis in which helically wound strands are selectively joined to one another at selected crossings of the strands, to favorably influence the combination of radial stiffness and axial bending flexibility.

Another object is to provide a stent or stent graft formed of helically wound strands with a desirable combination of a lower braid angle and enhanced radial stiffness.

A further object is to provide a process for manufacturing a medical device incorporating a plastically deformable stent or stent graft, that provides for a more uniform radial compression of the stent or stent graft about its deployment carrier, to reduce the risk of irregularities or distortions during such compression.

Yet another object is to provide a plastically deformable stent or stent graft that can be radially enlarged with relative ease, and after deployment has a high degree of resistance to radial compression and recoil.

SUMMARY OF THE INVENTION

To achieve these and other objects, there is provided a body insertable prosthesis. The prosthesis includes a plurality of helically strands forming a generally tubular structure. The strands further form multiple crossings of adjacent strands. The crossings include a plurality of secured crossings at which adjacent strands are joined, and a plurality of unsecured crossings at which the adjacent strands are free for limited travel relative to one another. The secured crossings, at least throughout a selected axial region of the tubular structure, are arranged in a pattern to selectively alter a radial stiffness of the tubular structure along the selected region. The tubular structure is radially enlargeable from a reduced-radius delivery state to a radially enlarged state to achieve contact with tissue at a treatment site within a body lumen.

Typically the pattern is selected to increase radial stiffness, preferably with little or no influence on axial bending stiffness so that the tubular structure remains maneuverable through curved internal passageways on its way to an intended treatment site. For example, the pattern can include a plurality of circumferencial rows or rings of secured crossings. Alternatively, the pre-determined pattern can be helical. It has been found particularly advantageous to use a helical pattern with a relatively large angle or steep pitch relative to a longitudinal axis of the prosthesis, in combination with a relatively small braid angle (gradual pitch) of the strands, to impart radial stiffness yet minimize the degree of axial shortening for a given radial enlargement of the prosthesis.

Suitable patterns can have a wide range of densities of secured crossings, with density being a ratio of the secured crossings to all of the crossings. Densities as low as 10% and as high as 90% can be employed. More preferably, the range of densities is 40–80%. A highly preferred density is about 4/9, or 44%.

The preferred manner of forming the secured crossings is by welding the adjacent strands. Resistance welding is particularly preferred, although other welding approaches may be used, e.g. laser welding (Nd: YAG Laser), ultrasonic welding and induction welding. Braising or soldering also may be used.

A pre-determined pattern of secured crossings can be formed over the entire length of a stent, or over the entire length except for the welding of all of the crossing at each end of the stent. Alternatively, the stent can incorporate a medial region and two opposed end regions, with a pre-determined pattern formed throughout the medial region and with the end regions having a higher density of secured crossings. In fact, all of the crossings throughout the end regions may be secured. This construction provides a favorable combination of maximum radial stiffness at the end regions, in combination with suitable flexibility for axial bending along the medial region. In one specific example of this construction, each end region consists of 4 to 6 rings or circumferencial "rows" of crossings, all welded or otherwise secured. The medial region includes a sequence of alternating secured and unsecured rings.

Further, in accordance with the present invention, there is provided a process for fabricating a prosthesis, including:

(a) forming a plurality of structural strands helically in a generally tubular configuration in which the strands cooperate to form multiple crossings of adjacent strands;

(b) bonding the adjacent strands at selected ones of the crossings, at least throughout a selected axial region along the tubular configuration, to form a pattern of welded crossings while leaving the adjacent strands at other crossings free for limited travel relative to one another.

A preferred manner of forming the strands into an open-frame configuration is to inter-braid the strands on a substantially cylindrical mandrel. After braiding, the strands can be annealed at a temperature of about 100° C. for about 30 minutes.

The selective welding can be accomplished with the braided tubular structure supported on a mandrel, usually a different mandrel than the one on which braiding is accomplished. Welding can be automated, involving a stepped rotation and axial translation of the mandrel and braided structure. Helical patterns are particularly preferred for automated welding, since the entire pattern can be formed as a single, linear sequence of welds.

The process further can include a radial compression of the completed stent or stent graft onto an inflatable balloon, or such balloon and the distal end of a catheter supporting the balloon. In particular, the balloon and tubular configuration can be inserted into an opening formed by an elongate elastic tubing member large enough to receive the braided structure and balloon prior to radial contraction. After insertion, the elastic tubing is contracted radially inwardly about the tubular structure, substantially uniformly along the length of the structure, to produce the necessary radial reduction. The even application of force minimizes the risk of producing unwanted distortions or irregularities during radial contraction. Also, the approach minimizes the tendency of the structure to axially elongate during radial contraction. This insures a corresponding reduction in the tendency to axially contract when the stent is radially enlarged during deployment.

There are several suitable approaches for controlling the elastic tubing member. According to one approach, the tubing member is disposed within a vacuum chamber, and enlarged against its elastic residual force by drawing a vacuum within the chamber. After insertion of the tubular structure, the chamber is allowed to return to normal pressure, allowing the elastic tubing member to contract about the structure.

In another approach, the elastic tubing is provided as an interior sleeve of an annular inflatable balloon-like member. The tubular welded structure and balloon it surrounds are inserted within the sleeve, with the annular inflatable member in a substantially aspirated condition. Then, the annular member is inflated, driving the sleeve radially inward to radially compress the tubular structure.

Thus in accordance with the present invention, stents and stent grafts, whether plastically deformable or self-expanding, can be formed with a selected pattern of secured crossings of the helical strands, to impart desirable radial stiffness and maintain axial bending flexibility. As compared to helically wound stents with connections only at their ends or with no secured connections, the selectively welded stents afford considerably enhanced radial strength and rigidity without undue resistance to axial bending. As compared to stents in which all of the crossings are secured, stents constructed according to the present invention afford more bending flexibility and maneuverability through tortuous vessels and other passages. Such maneuverability is further enhanced by the improved process for compressing the completed plastically deformable stent radially about an expansion balloon at the distal tip of a deployment catheter. Uniform compression during radial reduction reduces the risk of discontinuities or distortions that might interfere with travel through body lumens. Once positioned and radially enlarged at the treatment site, stents and stent grafts according to the present invention exhibit improved radial strength, good visibility under fluoroscopic techniques, and minimal recoil.

IN THE DRAWINGS

For a further appreciation of the above and other features and advantages, reference is made to the following detailed description and to the drawings, in which.

Figure 1:
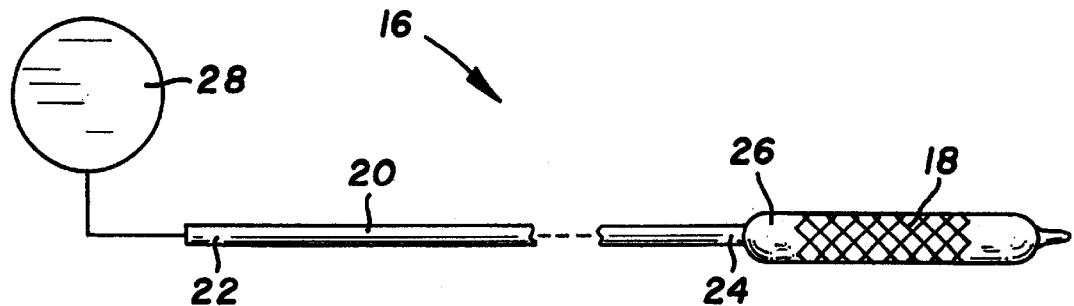
FIG. 1 is a schematic view of a stent deployment device carrying a stent constructed in accordance with the present invention.
Figure 2:
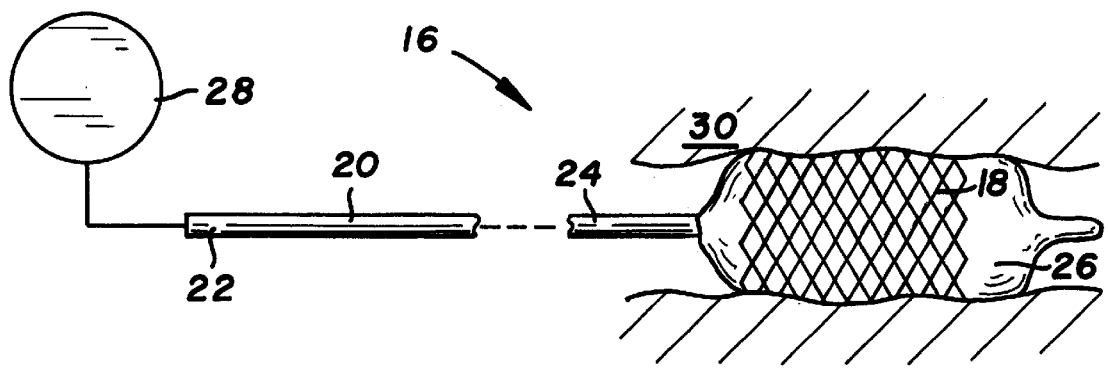
FIG. 2 is a schematic view similar to that of FIG. 1, showing the stent expanded to an enlarged-radius state.
Figure 3:
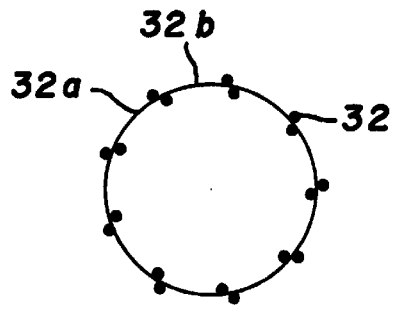
FIG. 3 is an enlarged end view of the stent.
Figure 4:
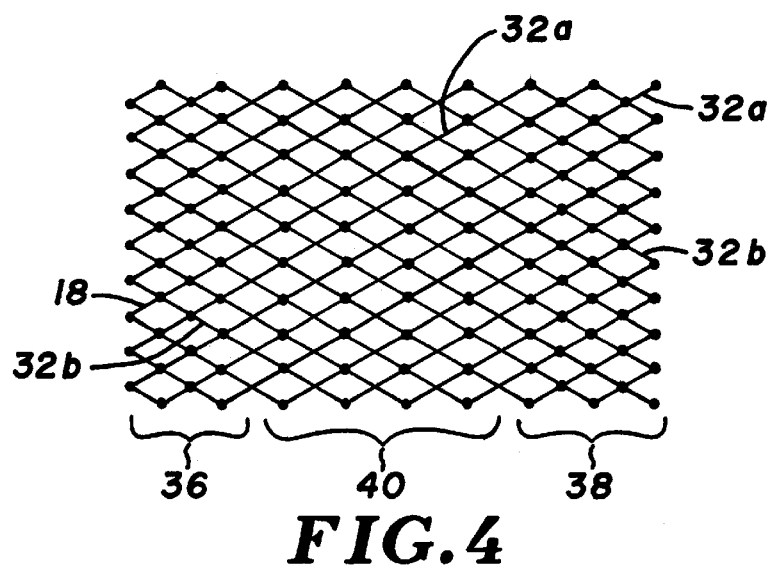
FIG. 4 is a side elevation of the stent, opened and lying flat, to more clearly show the strand arrangement and weld pattern.
Figure 16:
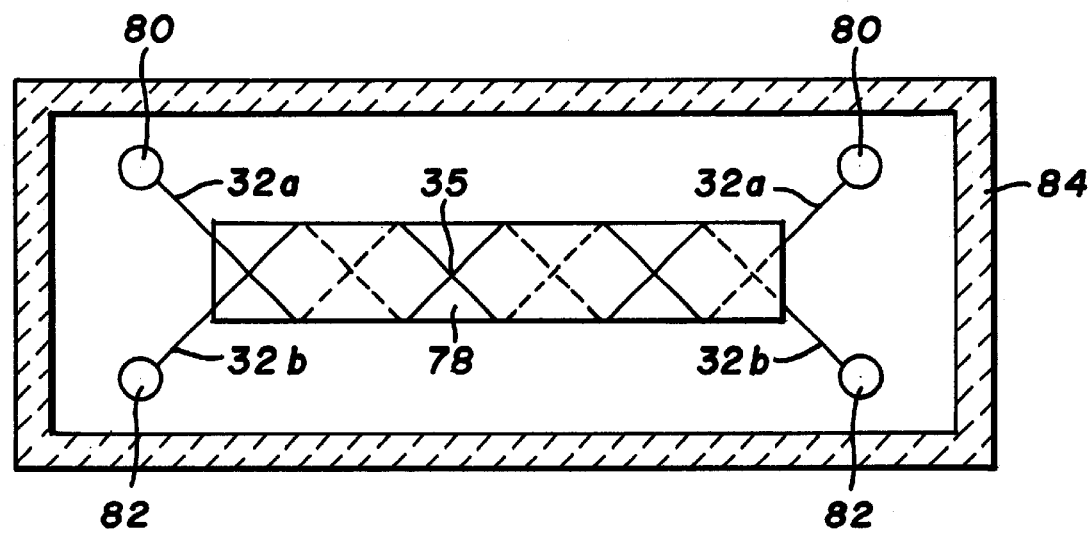
Figure 17:
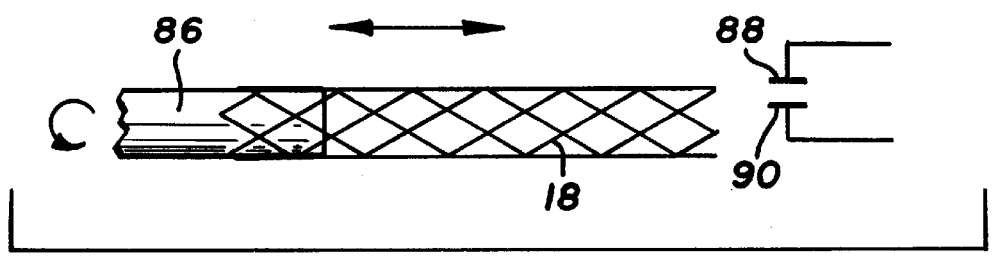
Figure 18:
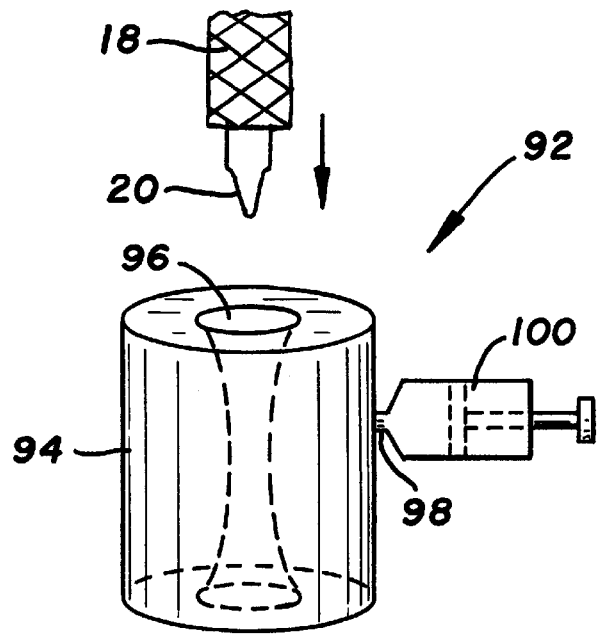
Figure 19:
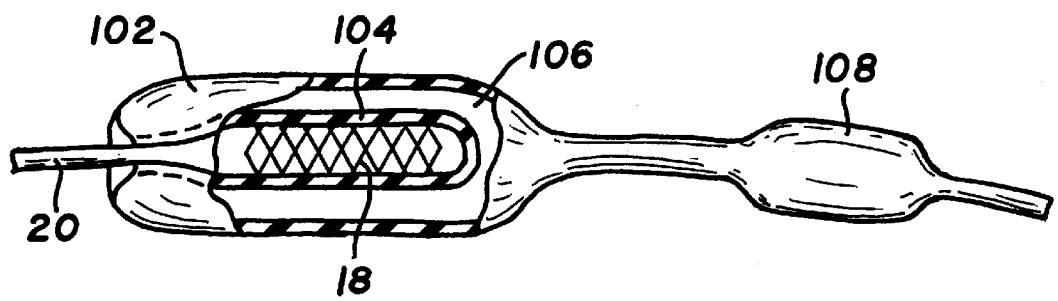
Figure 20:
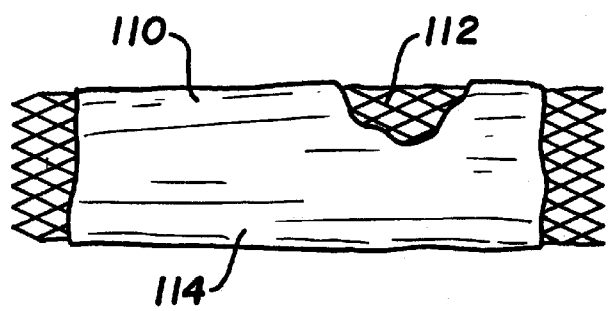

FIGS. 16 and 17 schematically illustrate a process for manufacturing the prosthesis of FIGS. 3 and 4;

FIGS. 18 and 19 schematically illustrate alternative approaches to the radial compression of the stent around the balloon and catheter of FIGS. 1 and 2; and FIG. 20 illustrates a stent graft constructed in accordance with the present invention.

DETAILED DESCRIPTION OF THE PREFERRED EMBODIMENTS

Turning now to the drawings, there is shown in FIGS. 1 and 2 a deployment device 16 for delivering a prosthesis, in particular a stent 18, to an intended fixation location or treatment site within a body lumen, and then radially enlarging the stent to fix the stent within the lumen.

The device includes an elongate and flexible catheter 20 constructed of a biocompatible polymer, e.g. polyurethane. A balloon inflation lumen (not shown) runs from a proximal end 22 of the catheter to a distal end 24 of the catheter, where the lumen is open to the interior of an elongate balloon 26 supported at the catheter distal end. At proximal end 22, the lumen is open to a source 28 of a balloon inflation fluid, e.g. a saline solution. Stent 18, radially compressed into a reduced-radius delivery state, surrounds balloon 26. Catheter 20 also incorporates a guidewire lumen, to facilitate advancing the balloon and catheter distally over a guidewire toward the intended treatment site. In the delivery state, stent 18 typically has a length in the range of 15–30 mm and a diameter of about 1.3 mm. The stent length and diameter can vary, depending oln the nature of the procedure and the size of the lumen.

After the catheter has been advanced sufficiently to place the balloon and stent at the treatment site, the balloon inflation fluid is supplied to the balloon under pressure, typically about three atmospheres to inflate balloon 26 and radially enlarge stent 18, thus expanding the stent into an intimate contact with surrounding tissue 30 as shown in FIG. 2. The enlarged stent can have a diameter of about 3 mm, or another suitable value within a range of about 2–6 mm. As it is radially enlarged, stent 18 undergoes an axial shortening by an amount that depends on the orientation of the strands or filaments of the stent as well as the amount of radial enlargement.

When the stent has been sufficiently enlarged, balloon 26 is aspirated by withdrawing the inflation fluid. Then, the balloon and catheter 20 are proximally withdrawn, leaving stent 18 at the treatment site.

Stent 18, shown in more detail in FIGS. 3 and 4, is of open-mesh or open-frame construction. More particularly, the stent is a latticework of helically wound strands 32 arranged in two oppositely directed and concentric sets of helices 32a and 32b. The helical strands are spaced apart axially from one another to define rhombotic interstices. Stent 18 is composed of eighteen strands, nine wound in each direction. Each strand runs the length of stent 18, and has a diameter of about 0.004 inches (0.1 mm). The strands are ductile, each being capable of elongation in the range of about 20–40 percent, more preferably about 30 percent. The stent is plastically deformable, due to the strand ductility. The strands preferably are formed of metal, with tantalum being the most preferred material for its body compatibility as well as ductility. Other, less preferred choices include gold, silver, titanium and 316 steel.

As seen in FIG. 3, the eighteen strands 32 come together in nine pairs of strands, secured to one another by welds 34. The same is true for the opposite end of stent 18. Between the ends of the stent, strands 32 form multiple crossings or intersections. At some of the crossings, the adjacent strands 32a and 32b are secured integrally to one another by a weld 34. The dots in FIG. 4 indicate welds 34. Other crossings 35 are unsecured, and the strands are free for limited movement relative to one another.

Figure 5:
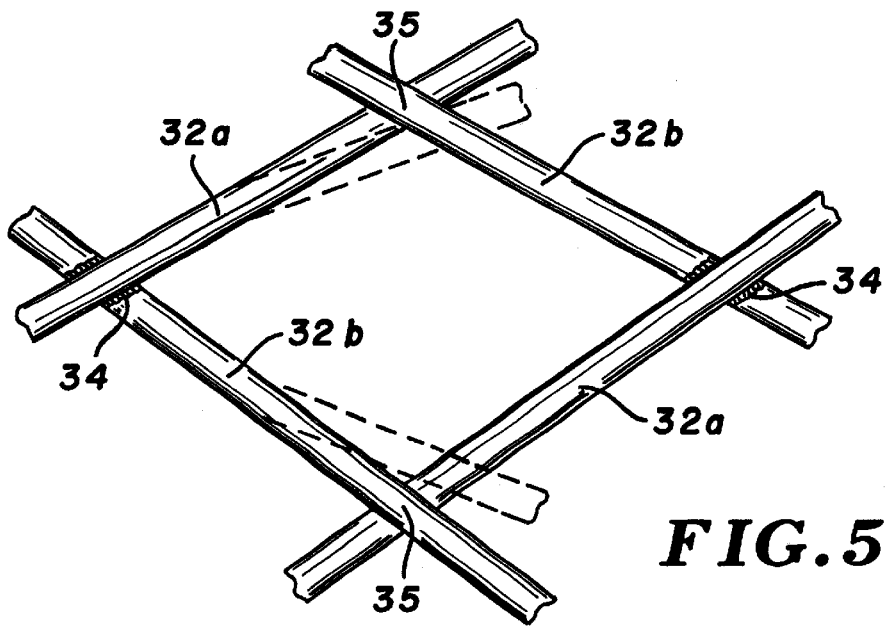
FIG. 5 is a further enlarged view of several strands of the stent.

The contrast between secured and unsecured strand crossings is seen from FIG. 5, where two of strands 32a and two of strands 32b are joined by two welds 34 and have two unsecured crossings. Broken lines, in greatly exaggerated fashion, illustrate the limited freedom of movement in strands 32a and 32b at the unsecured crossings.

Welds 34 are arranged in a selected pattern, to selectively influence the radial stiffness and the axial stiffness of stent 18. With reference to FIG. 4 once again, welds 34 conveniently are considered to be arranged in circumferential rows or rings, which appear as vertical rows in the flattened stent in the figure. The stent includes opposite end regions 36 and 38 where all of the crossings are secured. Between the end regions is a medial region 40, where the crossings are provided in alternating rings or circumferential rows of secured and unsecured crossings. This welding pattern has been found highly favorable because it provides substantial radial rigidity and strength, while also providing adequate axial flexibility (i.e. bending flexibility about transverse or radial axes) to facilitate distal advancement of the radially compressed stent and balloon 26 through serpentine or curved body passages on their way to the treatment site. The bending flexibility is provided by the alternating rows (rings) of unsecured crossings throughout medial region 40. Along end regions 36 and 38, all of the crossings are secured by welds 34, to further enhance radial strength and rigidity, thus to provide a more secure fixation of stent 18 at the treatment site.

A salient advantage of the invention resides in the radial stiffness provided by the welds, which enables a winding of helical strands 32 at substantially reduced braid angles. FIG. 4 illustrates a longitudinal axis 42 of stent 18. Each strand is wound at a pitch or angle $\alpha/2$ with respect to the longitudinal axis. In each case, the pitch is approximately 30 degrees. In stent 18 the helices are symmetrical. Consequently the braid angle $\alpha$ is twice the pitch, i.e. 60 degrees.

In stent designs in which the strands are joined, if at all, only at the ends of the stent, the strands themselves provide the radial strength and rigidity. Accordingly, achieving satisfactory radial strength requires large braid angles, preferably at least about 110 degrees (equivalent to pitches of 55 degrees). The greater the braid angle, the greater the radial strength for a given diameter stent construction and strand size. A disadvantage on the larger braid angles is that for a given radial expansion, the stent undergoes substantial axial shortening. Conversely, when the strands form smaller braid angles, a given radial enlargement of the stent results in substantially less axial shortening. More particularly, using welds to impart radial strength enables braid angles in the range of 30 degrees to 75 degrees (equivalent to a pitch in the range of 15–37.5 degrees), rather than braid angles of, for example, 110–140 degrees.

Figure 6:
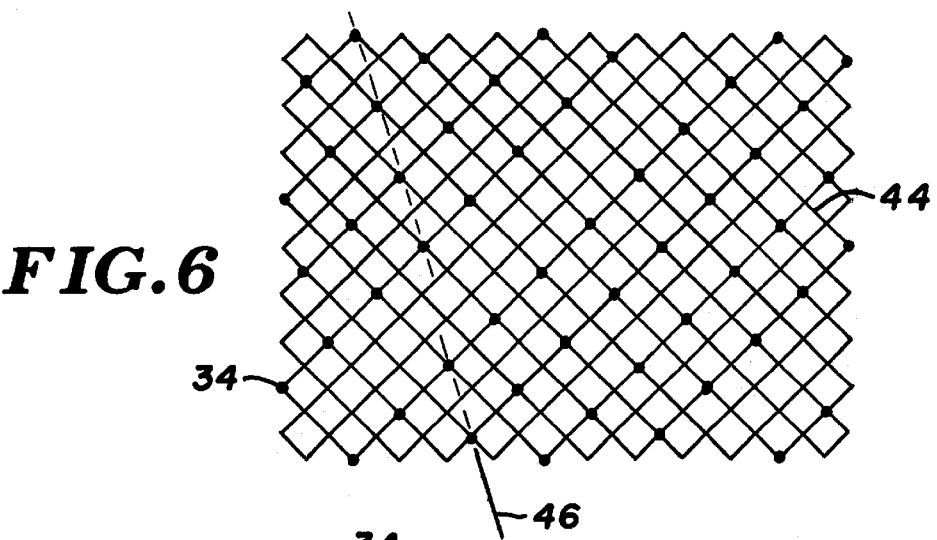
FIGS. 6–15 illustrate alternative embodiment stents, in each case with the stent opened and lying flat.

The above advantages are obtainable through a variety of weld patterns, as indicated by the following examples, all of which involve stents shown in an opened, flat condition to more clearly illustrate the strand arrangements and weld patterns:

FIG. 6 illustrates a stent 44 formed of 18 strands, 9 helically wound in each of two opposite directions. Welds 34 are formed at selected strand crossings, at a density of about ⅓, in terms of the ratio of welds to total crossings. As indicated by a line 46, welds 34 are arranged in a helical pattern with an effective pitch θ substantially greater (steeper) than the pitch α/2 of the strands. The higher effective pitch increases radial rigidity, as compared to a pattern of welds that matches the pitch of the strands.

Figure 7:
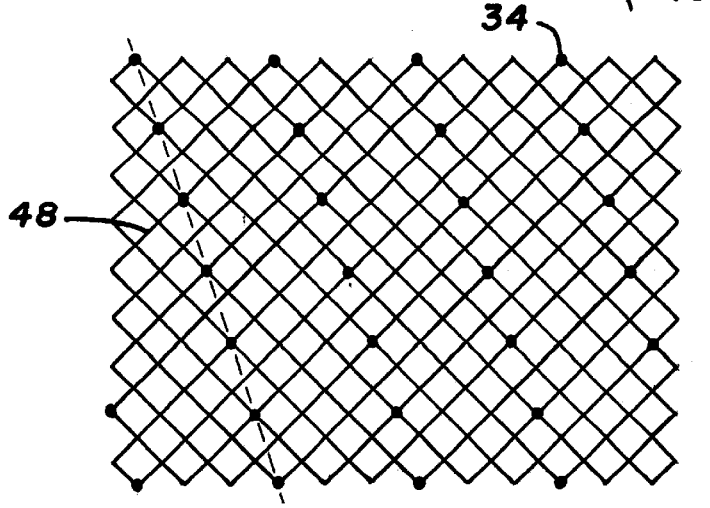

FIG. 7 illustrates a stent 48 formed of opposed sets of helical strands 32a and 32b, in which welds 34 again form a helical pattern. As compared to stent 44 in FIG. 6, adjacent turns of the helix formed by the welds are spaced apart from one another by a greater axial distance. This arrangement enhances axial bending flexibility, and like the arrangement in FIG. 6 extends for the entire axial length of the stent. The weld density is about ⅛.

Figure 8:
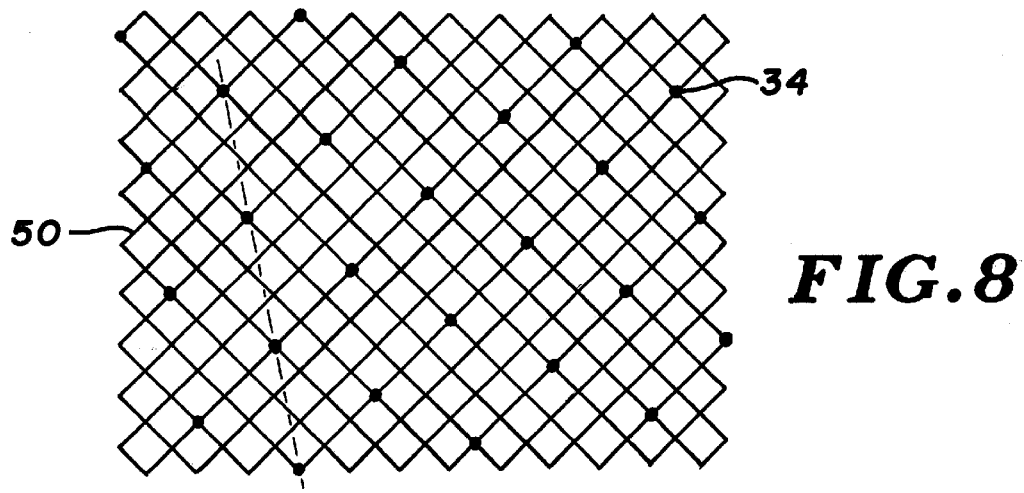

FIG. 8 shows a stent 50 formed of two sets of oppositely directed helical strands 32a and 32b. Welds 34 are arranged in a helical pattern. Once again, the weld density is about ⅛. However, in contrast to stent 48 in FIG. 7, the effective pitch of the pattern is steeper, and the axial spacing between adjacent turns of the helical pattern is reduced. The result, assuming other factors are equal, is greater radial rigidity and reduced axial bending flexibility.

Figure 9:
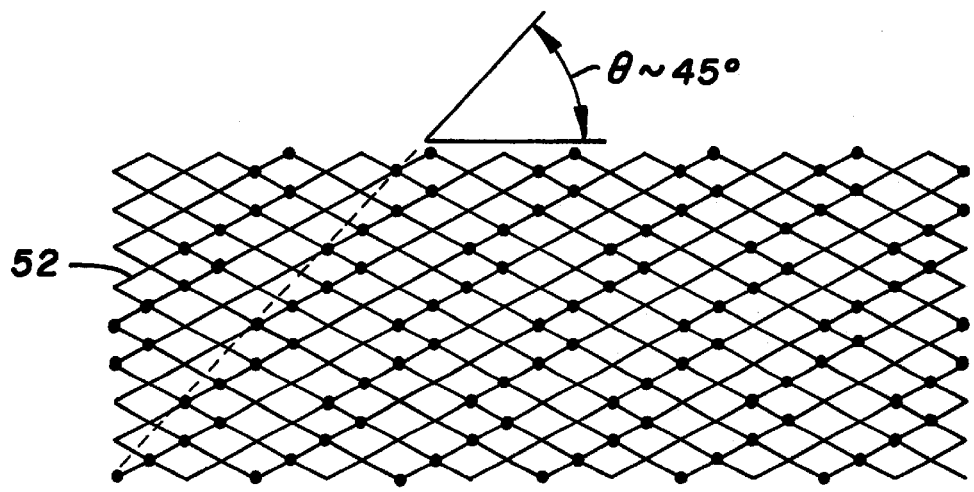

FIG. 9 illustrates a stent 52 formed of oppositely wound sets of helical strands 32a and 32b, in which welds 34 again form a helical pattern. The pattern differs from previously discussed helical embodiments, in that each turn of the helix includes several (in this case four) rows of welds, rather than one. The effective pitch θ of the pattern is about 45 degrees, as compared to the strand pitch α/2 of about 30 degrees.

Figure 10:
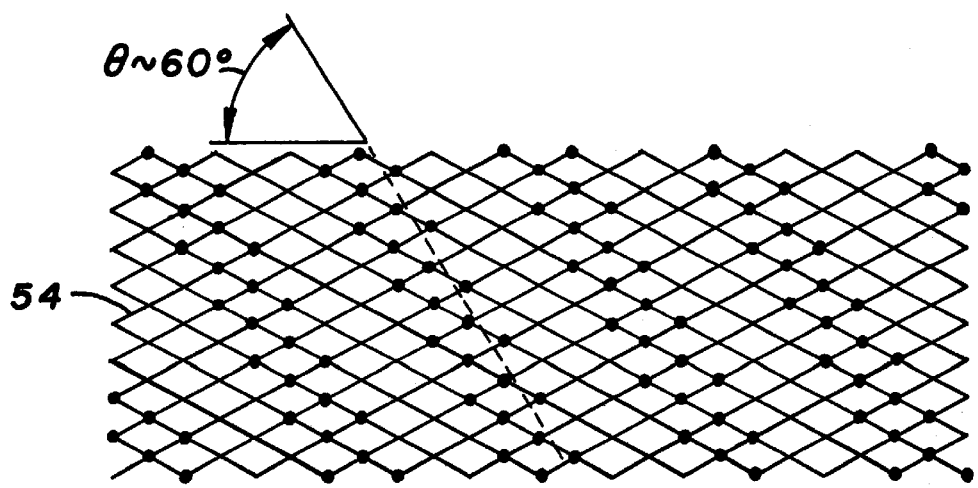

FIG. 10 illustrates another stent 54 having a helical pattern in which each turn of the pattern includes four parallel rows of welds 34. The effective pitch of θ the pattern is about 60 degrees, and is in the opposite direction from the pitch shown in FIG. 9.

Figure 11:
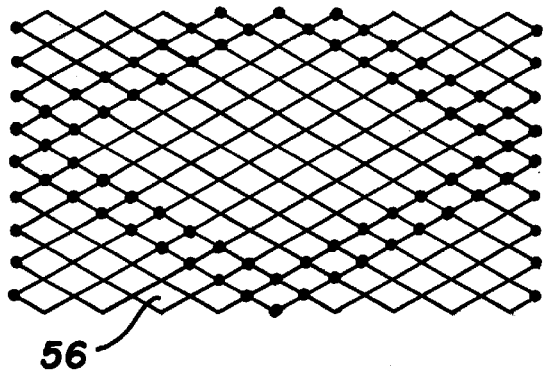

FIG. 11 illustrates a stent 56 composed of oppositely directed sets of helical strands 32a and 32b, in which the weld pattern resembles a diamond and includes two oppositely directed helices, each with an effective pitch of 30 degrees, matching the strand pitch. This weld pattern increases radial strength to a lesser extent as compared to the other patterns, but affords greater axial bending flexibility.

Figure 12:
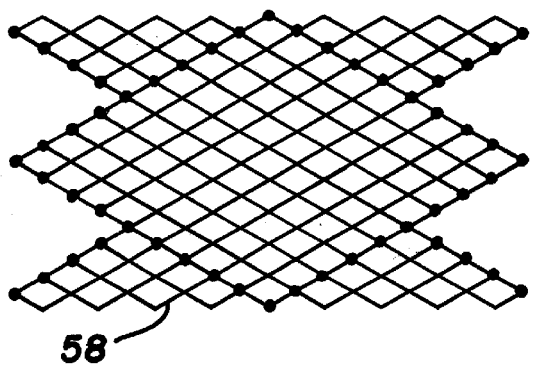

FIG. 12 illustrates a stent 58 formed of sets of oppositely directed helical strands 32a and 32b, with a weld pattern including helices in opposite directions, again at an effective pitch θ that matches the strand pitch α/2. The opposite ends of stent 58 are trimmed to correspond to the weld pattern, which reduces the number of welds required.

Figure 13:
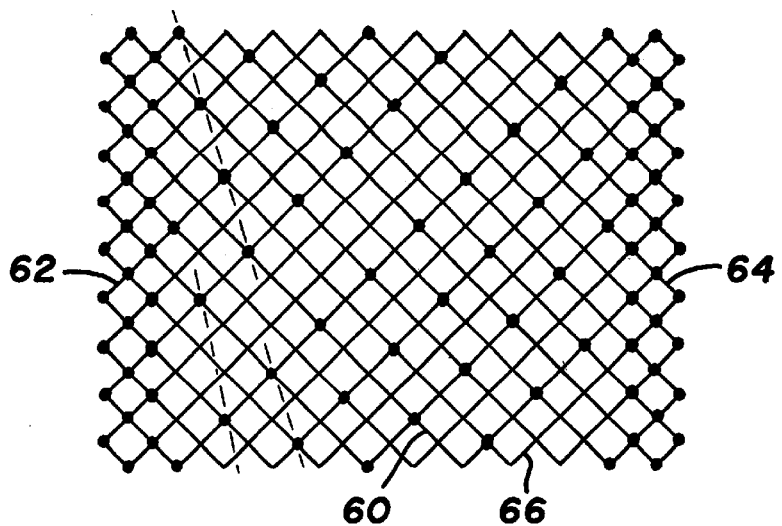

FIG. 13 illustrates a stent 60 including opposite end regions 62 and 64 with welds at all crossings, and a medial region 66 along which the welds form a helical pattern.

Figure 14:
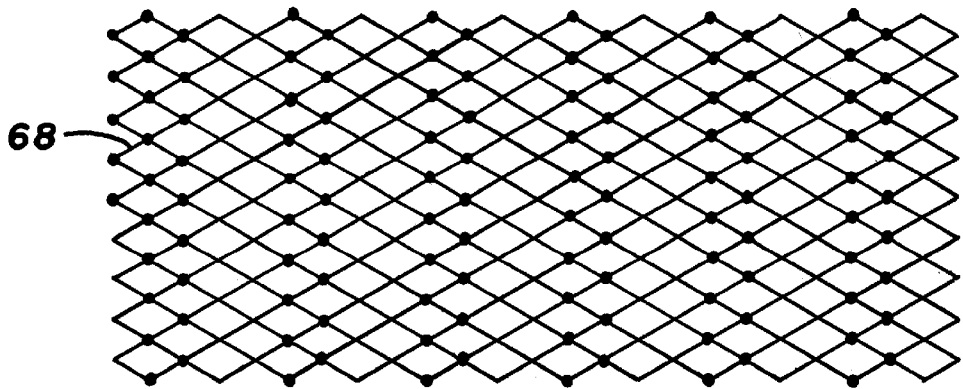

FIG. 14 illustrates an alternative embodiment stent 62 formed of oppositely directed sets of helically wound strands 32a and 32b. Welds 34 form a series of adjacent pairs of rings or circumferential rows, alternating with pairs of rings or rows of unsecured crossings. This arrangement provides a combination of radial rigidity and axial bending flexibility similar to stent 18 in FIG. 4, although stent 18 is more preferred.

Figure 15:
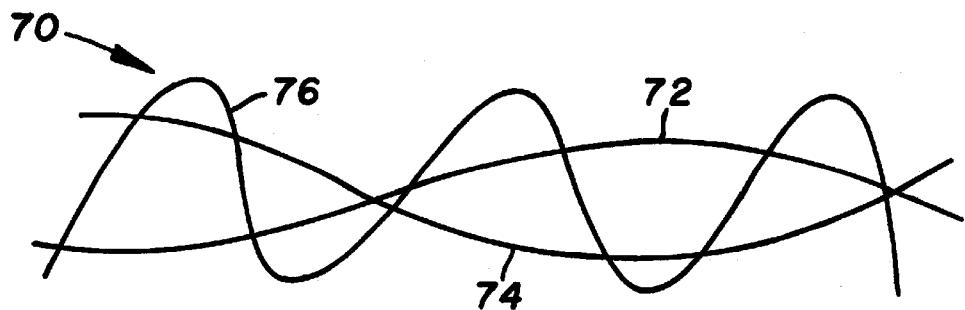

FIG. 15 illustrates a stent 70 formed of helically wound strands 72 and 74 wound at a relatively gradual pitch, combined with a strand 76 wound at a steeper pitch.

While the present invention has been discussed primarily in connection with plastically deformable stents, weld patterns likewise can be used to enhance the radial strength of radially self-expanding stents. In such stents the strands tend to be resilient rather than ductile, formed of materials such as cobalt-based alloys sold under the brand names "Elgioly" "Phynox" and "MP35N", as well as certain stainless spring steels. The resulting stents exhibit reduced axial shortening for a given degree of radial expansion, and have enhanced resistance to radial compression without sacrificing axial bending flexibility.

Further, stents according to the present invention can be formed of composite strands formed using DFT (drawn filled tubing) processes or the like, for example with a core of tantalum or of a titanium nickel alloy, surrounded by an Elgioly casing. The core preferably constitutes from about 25 percent to about 33 percent of the cross sectional area of the composite strand. The percentage is variable, based on the materials involved, to achieve a desired resiliency or ductility of the composite strand.

Stents constructed according to the present invention exhibit several advantages, regardless of whether they are of the plastically deformable or self-expanding type. These include greater visibility, because the helical winding construction results in a higher metal surface area as a percentage of the entire surface area of the stent. Compared with certain known configurations, e.g. the undulating configurations of the aforementioned '396 patent, stent fabrication is less complex. Further, the helical arrangement, in which the individual strands extend for the entire length of the stent, affords greater structural integrity, particularly when the stent is subjected to tensile stress.

Stent 18 exhibits an excellent resistance to recoil after radial expansion. More particularly, the external diameter of the stent, measured while balloon 26 was inflated, was 4.03 millimeters. After balloon deflation, the external diameter was measured at 3.98 millimeters, for a reduction in diameter of just 0.05 millimeters, the least among several stents tested. Stent 18 also exhibited superior radial rigidity. When tested for the hoop force in the collar sufficient to cause a 25% reduction in diameter from the original expanded diameter, stent 18 required the highest force, 0.18 lb. The highest value from among the other stents tested was 0.10 lb.

Stent 18 and the other stent embodiments shown in FIGS. 5–15, are fabricated first by interbraiding the sets of strands. FIG. 16 shows two structural strands (tantalum filaments) 32a and 32b, one from each set of oppositely directed structural strands, wound about a mandrel 78 and supported by respective bobbins 80 and 82. While just two strands are illustrated as a matter of convenience, all of the strands are wound about the mandrel and maintained together for shaping.

While wound about the mandrel, the tantalum strands are annealed within a furnace 84, preferably for about 30 minutes at a temperature of about 1100° C.

After annealing, the tubular structure composed of the strands is cleaned by washing or passivation, then mounted on another mandrel 86 for welding. As seen in FIG. 17, a resistance welding process is employed using electrodes 88 and 90 positionable on opposite sides of the adjacent strands at each crossing to be secured. Preferably the welding process is automatic, with successive welds accomplished in conjunction with stepped rotation and axial movement of the braided tubular structure. While the opposed sets of helical strands could simply overlie one another, an interbraiding of the strands is preferred, preferably according to a one-over-one pattern.

The preferred manner of welding is resistance welding, which uses pressure and heat generated due to the electrical resistance of the strands being joined. Preferably, the strands are joined using current and pressure settings appropriate for spot welding, without excessive formation of flash, while still forming a durable weld. Certain situations may call for weld penetration in excess of 20 percent, i.e. beyond the traditional definition of a spot weld. Variables such as weld current, hold time, hold cycles, the number of weld cycles, the electrode diameter and the electrode pressure or clamping force may require adjustment for best results. A consistent current path must be maintained, and a constant current mode is preferred. Also, heat treatment may be required after welding, to obtain optimum mechanical properties.

In preparing stent 18, welds were formed using a Unitek Miyachi Series 300 Weld Head System Model 350, and a Model HF2 two kilohertz high frequency resistance welding power supply. The electrodes are copper, and the mandrel is beryllium copper. Suitable currents are in the range of about 300–600 amperes, and clamping force is preferably within the range of 2–15 lb.

Laser welding is an alternative, e.g. using a Unitek/Benchmark Industries DE9000 50 W Nd: YAG laser. A single pulse mode is preferred, and a flow of argon gas preferably is maintained over the weld area. Welding pulse times can be 1.2–1.5 ms, more preferably 1.3 ms. Laser energy can ranged from about 0.6–1.5 J, preferably about 0.5 J; and power is in the range of 0.81–1.72 kW, preferably about 0.90 kW.

Another laser welding alternative is to use a $CO_2$ laser.

Strands 32 also may be joined by use of ultrasonic energy. The ultrasonic energy is used to cause mechanical vibrations at the interface of the strands, providing a friction weld.

Induction welding generates thermal energy within the strands by magnetic inductive heating, and may be the closest alternative to resistance welding.

Stent strands may be joined by braising or soldering, involving the use of a metal having a lower melting point to create the bond. A flux may be required.

Other possible alternatives include electron beam welding, which involves heating the strands with the kinetic energy of accelerated electrons, and affords the possibility of superior control over weld area and penetration; arc welding, with or without filler material; sinter bonding or solid state diffusion bonding, which may involve use of an interlayer; friction welding, involving galling of the interface between strands, due to their relative movement; and explosive bonding based on pressure shock waves.

In preparation for its eventual deployment, stent 18 must be reduced radially to the delivery state while positioned in surrounding relation to catheter 20 and balloon 26. The radial compression of stent 18 must be done with care, to avoid producing distortions or irregularities during radial contraction. To this end, a vacuum crimping tool 92, shown in FIG. 18, can be used to crimp the stent. Tool 92 includes a rigid cylinder 94 providing a vacuum chamber, and a length of elastomeric tubing 96 extending from one end of the cylinder to the other. Tubing 96 has an inner diameter approximately equal to that of balloon catheter 18. A connector 98 provides a path from the chamber to a syringe 100 or a vacuum pump capable of generating a vacuum within the cylinder. Drawing a vacuum within the cylinder causes a pressure imbalance, with elastomeric tubing 96 expanding radially in response to the imbalance.

When the vacuum (or partial vacuum) has sufficiently expanded tubing 96, e.g. to a 6 mm diameter, catheter 20 and balloon 26, along with stent 18 in surrounding relation to the balloon, are inserted into elastomeric tubing 96. Then, the vacuum is released, causing tubing 96 to contract under its residual elastic force, to compress stent 18 firmly onto the balloon. After stent compression, the vacuum is reapplied and the stent, catheter and balloon are withdrawn from the elastomeric tubing.

FIG. 19 illustrates an alternative tool 102 for using pressure in lieu of a vacuum to radially compress the stent. More particularly, the tool is an inflatable balloon-like member having an internal sleeve 104 for receiving the catheter, balloon and surrounding stent, and an annular chamber 106 surrounding the sleeve. A bulb 108 is operable to inflate member 102 after the catheter, balloon and stent have been inserted into sleeve 104. Inflation radially compresses the sleeve, thus to compress the stent. Following compression, the inflatable member is aspirated to release the catheter, balloon and stent.

FIG. 20 illustrates a stent graft 110 including a structural layer 112 formed of interbraided strands 32 selectively welded according to the present invention. Layer 112 supports a graft layer 114 that is substantially impervious to blood and other body fluids. Graft layer 114, for example, can be formed of interwoven multifilament yarns. Suitable materials include PET, polypropylene, polyurethane, polycarbonateurethane, HDPE, polyethylene, silicone, PTFE, ePTFU, and polyolefin. Stent graft 110 is particularly well suited for fixation within a blood vessel to shunt blood past an aneurysm, and alternatively can be used to structurally support weakened portions of other body lumens.

Thus in accordance with the present invention, stents and stent grafts are formed of helical strands welded at selected crossings or intersections, to provide weld patterns that enhance radial rigidity without significantly reducing axial bending flexibility, or otherwise favorably influence said characteristics. The use of welds to increase radial strength enables the winding of opposed helical strands at substantially reduced braid angles, reducing the degree of axial shortening for a given amount of radial enlargement of the stent. The stent exhibits virtually no recoil after its fixation, and also exhibits a high radial resistance to compression, and good visibility when fluoroscopic techniques are employed.

The patents and any other publications discussed herein are incorporated by reference, each in its entirety and for all purposes.

What is claimed is:

1. A process for fabricating a prosthesis, including:
   forming a plurality of structural strands helically in a generally tubular configuration to provide a generally tubular structure in which the strands cooperate to form multiple crossings of adjacent strands;
   bonding the adjacent strands at selected ones of the crossings, at least throughout a selected axial region along the tubular configuration, to form a pattern of bonded crossings while leaving the adjacent strands at other crossings free for limited travel relative to one another.

2. The process of claim 1 further including:
   after said bonding, cutting the tubular configuration to a selected length.

3. The process of claim 1 wherein:
   said forming of the strands into a tubular configuration includes interbraiding the strands on a substantially cylindrical mandrel.

4. The process of claim 3 further including:
   after said braiding, heat treating the braided strands to anneal the strands.

5. The process of claim 4 wherein:
   the annealing comprises maintaining the strands at a temperature of about 1100° C. for approximately 30 minutes.

6. The process of claim 1 wherein:
the bonding step includes supporting the tubular structure on a mandrel.

7. The process of claim 1 further including:
inserting an elongate inflatable balloon axially into the tubular structure, so that the tubular structure over substantially its entire length surrounds the balloon; and
with the tubular structure surrounding the balloon, plastically deforming the strands to radially contract the tubular structure about the balloon, while maintaining the balloon in a substantially aspirated condition.

8. The process of claim 7 wherein:
the contraction of the tubular structure comprises providing an elastic tubing member forming an opening sufficiently large to receive the tubular structure and balloon prior to said radial contraction; inserting the balloon and tubular structure into the opening; and contracting the elastic tubing member radially inwardly about the tubular structure and substantially uniformly along the length of the tubular structure.

9. The process of claim 8 wherein:
the tubing member is formed as an interior sleeve portion of an annular inflatable shaping member; and said contraction comprises inserting the tubular configuration and balloon into the opening while the inflatable member is substantially aspirated, then inflating the inflatable member to radially compress the tubular configuration.

10. The process of claim 8 wherein:
the tubing member is disposed within a vacuum chamber and is radially enlargeable responsive to at least a partial evacuation of the chamber; and
wherein the contraction of the tubular configuration comprises generating at least a partial vacuum in the chamber, inserting the tubular configuration and balloon into the opening during vacuum generation, and releasing the vacuum to allow the tubing member to radially compress the tubular configuration.

11. The process of claim 1 wherein:
said bonding of the adjacent strands comprises one of the following: resistance welding, induction welding, laser welding, ultrasonic welding, braising, and soldering.

12. A process for fabricating a prosthesis, including:
providing a radially expandable and radially contractible tubular structure;
inserting an elongate inflatable balloon axially into the tubular structure, so that the tubular structure surrounds the balloon;
providing an elastic tubing member formed as an interior sleeve portion of an inflatable shaping member, with the elastic tubing member forming an opening sufficiently large to receive the tubular structure;
with the tubular structure surrounding the balloon and with the inflatable shaping member substantially aspirated, inserting the tubular structure and the balloon into the opening so that the elastic tubing member surrounds the tubular structure; and
with the elastic tubing member surrounding the tubular structure and the balloon, and while maintaining the balloon in a substantially aspirated condition, inflating, the inflatable shaping member to urge the elastic tubing member radially inwardly about the tubular structure and substantially uniformly along the length of the tubular structure, plastically deforming the tubular structure to radially contract the tubular structure about the balloon.

13. The process of claim 12 wherein:
said tubular structure is formed of a plurality of structural strands, and said providing the radially expandable and radially contractible tubular structure comprises forming the plurality of structural strands helically and with multiple crossings of adjacent strands.

14. The process of claim 13 further including:
bonding the adjacent strands at selected ones of the crossing, at least throughout a selected axis region along the tubular structure, to form a pattern of bonded crossings while leaving the adjacent strands at other crossings free for limited travel relative to one another.

15. The process of claim 14 wherein:
said forming the plurality of structural strands includes interbraiding the structural strands on substantially cylindrical mandrel.

16. The process of claim 15 further including:
after interbraiding the strands, heat treating the interbraided strands to anneal the strands.

17. The process of claim 12 further including:
after radially contracting the tubular structure about the balloon, aspirating the inflatable shape member to release the tubular structure and the balloon.

18. The process of claim 12 wherein:
the tubular structure, when inserted into the opening of the elastic tubing member, is surrounded over substantially its entire length by the elastic tubing member.

19. The process of claim 12 wherein:
said elongate inflatable balloon is disposed along a distal end region of a catheter;
said inserting the elongate inflatable balloon axially into the tubular structure comprises disposing the tubular structure about the distal end region of the catheter; and
said inserting the tubular structure and balloon into tile opening of the elastic tubing member comprises inserting the distal end of the catheter into said opening.

20. The process of claim 12 wherein:
said tubular structure is formed of at least one structural strand.

21. A process for fabricating a prosthesis, including:
forming a plurality of structural strands helically and with multiple crossings of adjacent strands, to provide a radially expandable and radially contractible tubular structure;
bonding the adjacent strands at selected ones of the crossings, at least throughout a selected axial region along the tubular structure, to form a pattern of bonded crossings while leaving the adjacent strands at other crossings free for limited travel relative to one another;
inserting an elongate inflatable balloon axially into the tubular structure, so that the tubular structure surrounds the balloon;
providing an elastic tubing member that forms an opening sufficiently large to receive the tubular structure;
with the tubular structure surrounding the balloon, inserting the tubular structure and the balloon into the opening so that the elastic tubing member surrounds the tubular structure; and
with the elastic tubing member surrounding the tubular structure and the balloon, and while maintaining the balloon in a substantially aspirated condition, urging the elastic tubing member radially inwardly about the tubular structure and substantially uniformly along the length of the tubular structure, plastically deforming the tubular structure to radially contract the tubular structure about the balloon.

22. The process of claim 21 wherein:

the elastic tubing member is formed as an interior sleeve portion of an annular inflatable shaping member;

the balloon and tubular structure are inserted into the opening while the inflatable shaping member is substantially aspirated; and said urging the elastic tubing member comprises inflating the inflatable shaping member.

23. The process of claim 22 further including:

after radially urging the tubular structure about the balloon, aspirating the inflatable shaping member to release the tubular structure and the balloon.

24. The process of claim 21 wherein:

said forming the plurality of structural strands includes interbraiding the structural strands on a substantially cylindrical mandrel.

25. The process of claim 24 further including:

after interbraiding the structural strands, heat treating the interbraided strands to anneal the strands.

26. The process of claim 21 wherein:

the tubular structure, when inserted into the opening of the elastic tubing member, is surrounded over substantially its entire length by the elastic tubing member.

27. The process of claim 21 wherein:

said elongate inflatable balloon is disposed along a distal end region of a catheter;

said inserting the elongate inflatable balloon axially into the tubular structure comprises disposing the tubular structure about the distal end region of the catheter; and said inserting the tubular structure and balloon into the opening of the elastic tubing member comprises inserting the distal end of the catheter into said opening.

28. The process of claim 21 wherein:

said bonding comprises welding the adjacent strands at the selected crossings.

29. The process of claim 21 wherein:

the elastic tubing member is disposed within a vacuum chamber and is radially enlargeable responsive to generating at least a partial evacuation of the vacuum chamber;

the balloon and tubular structure are inserted into the opening during the at least partial evacuation of the vacuum chamber; and the urging of the elastic tubing member radially inwardly about the tubular structure comprises releasing the at least partial vacuum to allow the elastic tubing member to radially contract about the tubular structure.

* * * * *